(12) United States Patent
Ackerson et al.

(10) Patent No.: US 8,674,474 B2
(45) Date of Patent: Mar. 18, 2014

(54) BIOSENSORS INTEGRATED WITH A MICROFLUIDIC STRUCTURE

(71) Applicant: International Business Machines Corporation, Armonk, NY (US)

(72) Inventors: Kristin M. Ackerson, Colchester, VT (US); John J. Ellis-Monaghan, Grand Isle, VT (US); Jeffrey P. Gambino, Westford, VT (US); Yen L. Lim, Essex Junction, VT (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/033,615

(22) Filed: Sep. 23, 2013

(65) Prior Publication Data

US 2014/0021516 A1    Jan. 23, 2014

Related U.S. Application Data

(62) Division of application No. 13/293,795, filed on Nov. 10, 2011, now Pat. No. 8,551,859.

(51) Int. Cl.
*H01L 21/70* (2006.01)
*H01L 21/76* (2006.01)

(52) U.S. Cl.
USPC ............................ 257/522; 438/422

(58) Field of Classification Search
USPC .................. 438/319, 411, 422, 619; 257/522
See application file for complete search history.

(56) References Cited

U.S. PATENT DOCUMENTS

| | | | |
|---|---|---|---|
| 6,872,656 B2 | 3/2005 | Sakai | |
| 7,667,559 B2 | 2/2010 | Yamanaka et al. | |
| 8,097,483 B2 | 1/2012 | Van Schaijk et al. | |
| 8,551,859 B2 * | 10/2013 | Ackerson et al. | 438/422 |
| 2011/0315527 A1 | 12/2011 | Dang et al. | |

OTHER PUBLICATIONS

Shin, J. et al., "FET-based Biosensors for Detection of Biomolecules", Extended Abstracts of the 2008 International conference on Solid State Devices and Materials, Tsukuba, 2008, pp. 744-745.
Han, S. et al., "CMOS Intergrated DNA Microarray Based on GMR Sensors", Stanford University, 2006, 4 pages.
Sakata, T. et al., "DNA Analysis Chip Based on Field-Effect Transistors", Japanese Journal of Applied Physics, vol. 44, No. 4B, 2005, pp. 2854-2859.

* cited by examiner

*Primary Examiner* — Calvin Lee
(74) *Attorney, Agent, or Firm* — Michael Le Strange; Roberts Mlotkowski Safran & Cole, P.C.

(57) ABSTRACT

A biosensor with a microfluidic structure surrounded by an electrode and methods of forming the electrode around the microfluidic structure of the biosensor are provided. A method includes forming a gate or electrode in a first layer. The method further includes forming a trench in a second layer. The method further includes forming a first metal layer in the trench such that the first metal layer is in electrical contact with the gate or the electrode. The method further includes forming a sacrificial material in the trench. The method further includes forming a second metal layer over the sacrificial material and in contact with the first metal layer. The method further includes removing the sacrificial material such that a microfluidic channel is formed surrounded by the first and the second metal layers.

12 Claims, 13 Drawing Sheets

US 8,674,474 B2

BIOSENSORS INTEGRATED WITH A MICROFLUIDIC STRUCTURE

This application is a divisional of U.S. patent application Ser. No. 13/293,795, filed Nov. 10, 2011, now U.S. Pat. No. 8,551,859 issued Oct. 8, 2013, the disclosure of which is incorporated herein in its entirety by reference.

FIELD OF THE INVENTION

The invention relates to biosensors integrated with a microfluidic structure and, more particularly, to biosensors with a microfluidic structure surrounded by an electrode and methods of forming the electrode around the microfluidic structure of the biosensor.

BACKGROUND

A biosensor is a device for measuring the concentration of an analyte in a biological sample. A typical biosensor comprises a sensitive biological recognition element able to interact specifically with a target analyte, and a transducer or detector element that is able to transform the recognition event of the analyte with the biological element into a measurable signal. In contrast with conventional bioassays, biosensors allow the detection of molecular interactions as they take place, without requiring auxiliary procedures, making them highly attractive for biotechnological applications.

Among the various types of biosensors, field-effect transistor (FET) biosensors provide advantages in terms of miniaturization, standardization, mass-production, and a suitable configuration in which both the sensors and measurement circuits are integrated on the same chip. The FET biosensors, e.g., genetic FET biosensors, are particularly suited for the detection of charged biomolecules such as deoxyribonucleic acid (DNA).

In particular, the principle of genetic FET biosensors is based on the detection of a charge density change on the gate surface of the genetic FET, which is induced by the specific binding of DNA molecules to oligonucleotides probes. For instance, oligonucleotides probes are immobilized on the surface of a gate insulator of the genetic FET. When the genetic FET is immersed in a measurement solution comprising complementary DNA molecules, hybridization occurs at the surface of the gate area between the DNA molecules and the immobilized oligonucleotides. Since DNA molecules are negatively charged in an aqueous solution, the hybridization event can be detected by measuring a shift of the threshold voltage ($V_t$).

In order to achieve efficient immersion of the surface of the electrode area with the measurement solution, the electrode area of the genetic FET is typically integrated with a microfluidic channel for containing a flowing measurement solution. Nonetheless, molecular recognition events such as the hybridization and interaction of the charged biomolecules on the surface of the FET may be unreliable for the detection of certain analytes.

Accordingly, there exists a need in the art to overcome the deficiencies and limitations described hereinabove.

SUMMARY

In a first aspect of the invention, a method of forming a biosensor is provided. The method comprises forming a gate or electrode in a first layer. The method further comprises forming a trench in a second layer. The method further comprises forming a first metal layer in the trench such that the first metal layer is in electrical contact with the gate or the electrode. The method further comprises forming a sacrificial material in the trench. The method further comprises forming a second metal layer over the sacrificial material and in contact with the first metal layer. The method further comprises removing the sacrificial material such that a microfluidic channel is formed surrounded by the first and the second metal layers.

In another aspect of the invention, a method of forming a biosensor is provided. The method comprises forming a gate or electrode in a first layer. The method further comprises forming a contact and a wiring layer in a second layer. The method further comprises forming a trench in a third layer. The method further comprises forming a first metal layer in the trench such that the first metal layer is in electrical contact with the gate or the electrode via the contact and the wiring layer. The method further comprises forming a sacrificial material in the trench. The method further comprises forming a second metal layer over the sacrificial material and in contact with the first metal layer. The method further comprises forming a capping layer over metal layer and the sacrificial material. The method further comprises forming a vent hole in the capping layer. The method further comprises removing the sacrificial material through the vent hole such that a microfluidic channel is formed surrounded by the first and the second metal layers.

In yet another aspect of the invention, a biosensor is provided. The biosensor comprises a gate or electrode in a first layer. The biosensor further comprises a trench in a second layer. The biosensor further comprises a first metal layer in a first portion of the trench that is in electrical contact with the gate or the electrode. The biosensor further comprises a second metal layer formed over the first portion of the trench and that is in electrical contact with the first metal layer. The biosensor further comprises that the first metal layer and the second metal layer surround the first portion of the trench and form at least a portion of a microfluidic channel for the biosensor.

In another aspect of the invention, a design structure tangibly embodied in a machine readable storage medium for designing, manufacturing, or testing an I-MOS is provided. The design structure comprises the structures of the present invention. In further embodiments, a hardware description language (HDL) design structure encoded on a machine-readable data storage medium comprises elements that when processed in a computer-aided design system generates a machine-executable representation of the biosensor structure, which comprises the structures of the present invention. In still further embodiments, a method in a computer-aided design system is provided for generating a functional design model of the biosensor structure. The method comprises generating a functional representation of the structural elements of the biosensor structure.

BRIEF DESCRIPTION OF THE SEVERAL VIEWS OF THE DRAWINGS

The present invention is described in the detailed description, which follows, in reference to the noted plurality of drawings by way of non-limiting examples of exemplary embodiments of the present invention.

DETAILED DESCRIPTION

The invention relates to biosensors integrated with a microfluidic structure and, more particularly, to biosensors with a microfluidic structure surrounded by an electrode and methods of forming the electrode around the microfluidic structure of the biosensor. More specifically, implementations of the invention provide a biosensor structure on a chip and a method of manufacturing the biosensor structure on the chip such that an electrode of a FET surrounds the microfluidic channel.

Advantageously, the biosensor and method of manufacturing the biosensor increases the surface area of the electrode exposed to the measurement solution in the microfluidic channel. The increase in surface area of the electrode being exposed to the measurement solution enables greater molecular recognition events such as the hybridization and interaction of the charged or magnetized biomolecules on the gate, and thus an increased measurable shift of the threshold voltage ($V_t$) for the biosensor. In addition, advantageously, the biosensor and method of manufacturing the biosensor provide a less expensive and more portable means for detecting and measuring the concentration of an analyte over traditional means, e.g., fluorescence.

Figure 1A:
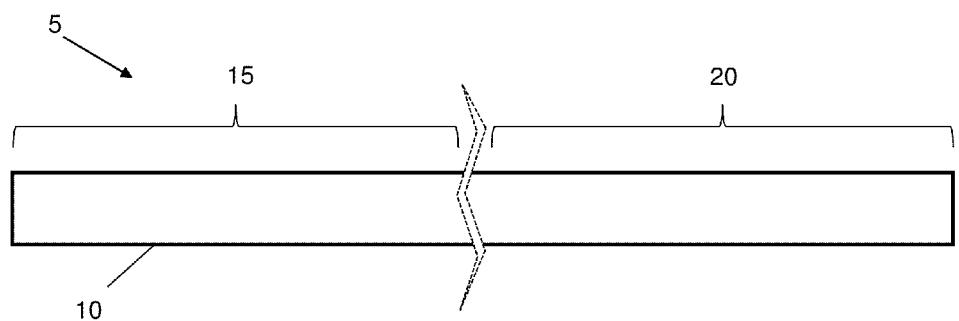
FIGS. 1a, 1b, 2, 3, 4a, 4b, 5-9, 10a, 10b, 11, 12a, 12b, 13a, and 13b show processing steps and respective structures in accordance with aspects of the present invention.

FIGS. 1a, 1b, 2, 3, 4a, 4b, 5-9, 10a, 10b, 11, 12a, 12b, 13a, and 13b show processing steps and resultant structures in accordance with embodiments of the invention. Specifically, FIG. 1a shows a biosensor structure 5 comprising a wafer 10. In embodiments, the wafer 10 may comprise a bulk silicon or silicon on insulator (SOI) wafer. More specifically, FIG. 1a shows an exemplary SOI wafer 10 employed as an intermediate structure in implementations of the invention. The SOI wafer 10 may be fabricated using techniques well known to those skilled in the art. For example, the SOI wafer 10 may be formed by conventional processes including, but not limited to, oxygen implantation (e.g., SIMOX), wafer bonding, etc. In embodiments, the SOI wafer 10 has a thickness of about 700 μm; however, the invention is not limited to these dimensions, and the various portions of the SOI wafer 10 may have any desired thicknesses.

Figure 1B:
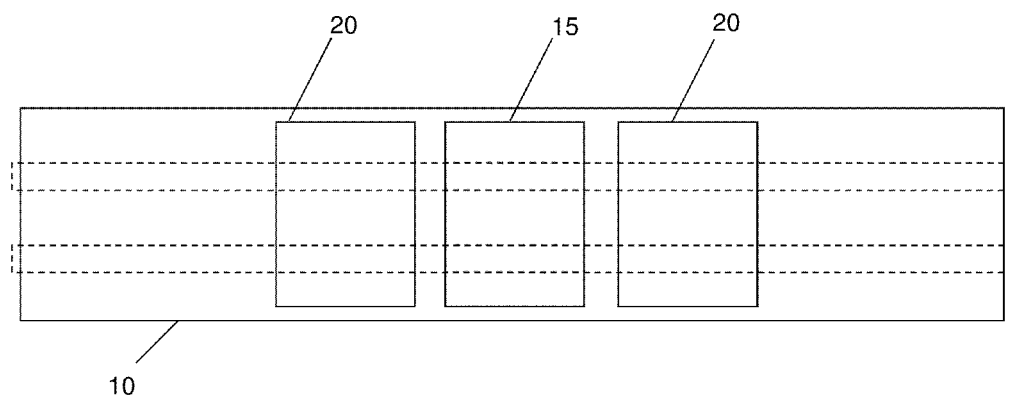

As shown in FIGS. 1a and 1b, the SOI wafer 10 may comprise multiple areas upon which a gate electrode and a reference electrode may be built either simultaneously or at separate stages of manufacture. For example, the SOI wafer 10 may comprise a gate electrode 15 formed in a first area of the wafer and a reference electrode 20 formed in a second area of the wafer. However, the biosensor structure 5 is not limited to only one gate electrode and one reference electrode, and the gate electrode 15 and the reference electrode 20 are only being used as illustrative of the invention for ease of understanding the invention.

Figure 2:
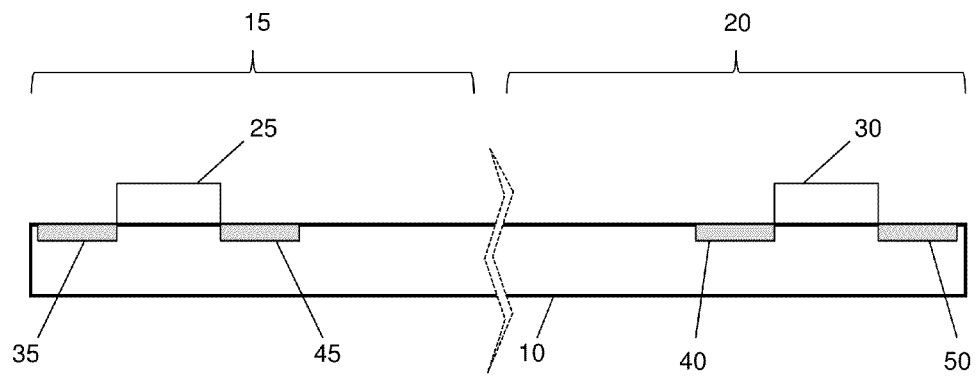

As shown in FIG. 2, gates 25 and 30 are formed on the SOI wafer 10. For example, the gate 25 is formed as a part of the gate electrode 15 and the gate 30 is formed as a part of the reference electrode 25. In embodiments, the gates 25 and 30 may comprise a gate body (e.g., gate conductor), a gate dielectric, and a gate cap, and may be fabricated by conventional processes such as deposition, lithographic, and etching processes, known to those of skill in the art.

Following formation of the gates 25 and 30, first doped regions 35 and 40 (e.g., N+ drain) are formed in the SOI wafer 10 adjacent the gates 25 and 30. For example, the first doped region 35 is formed as a part of the gate electrode 15 and the first doped region 40 is formed as a part of the reference electrode 15. The first doped regions 35 and 40 may be formed using any suitable doping technique, such as ion-implantation.

Second doped regions 45 and 50 (e.g., P+ source) are formed in the SOI wafer 10 adjacent the gates 45 and 50. For example, the second doped region 45 is formed as a part of the gate electrode 15 and the second doped region 50 is formed as a part of the reference electrode 25. The second doped regions 45 and 50 may be formed using any suitable doping technique, such as ion-implantation. In alternative embodiments, electrodes may be formed in the wafer 10 in substitution of the gates with first and second doped regions.

Figure 3:
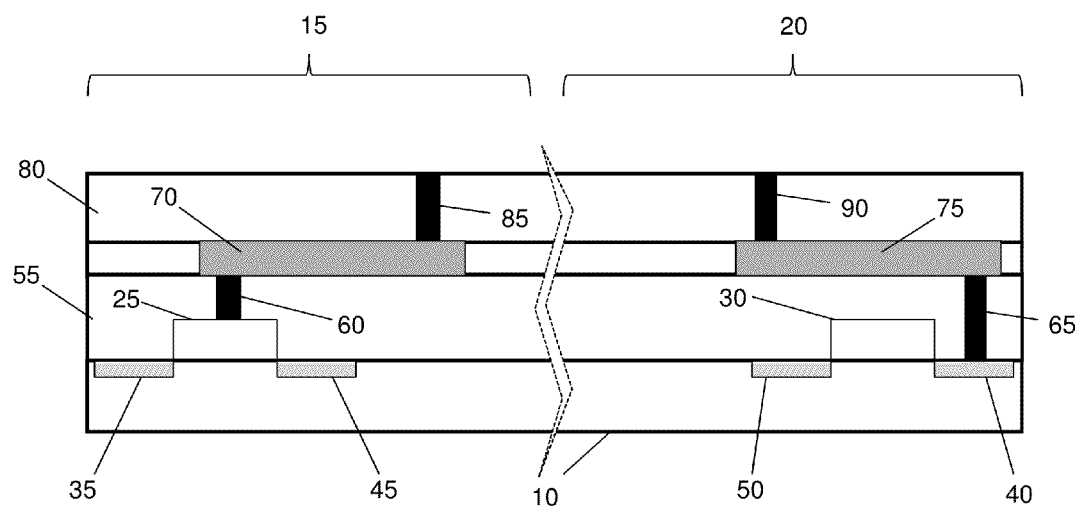

As shown in FIG. 3, back-end-of-line (BEOL) processes may be performed on the structure shown in FIG. 2. For example, as shown in FIG. 3, an interlevel dielectric (ILD) layer 55 may be deposited on the exposed surfaces and planarized. The ILD layer 55 may comprise any suitable dielectric material, for example, $SiO_2$, TEOS, borophosphosilicate glass (BPSG), high density plasma (HDP) oxide, etc. The ILD layer 55 may be deposited in any suitable manner such as chemical vapor deposition (CVD) and may be planarized using chemical-mechanical planarization (CMP).

As further depicted in FIG. 3, contacts 60 and 65 may be formed in the ILD layer 55 to the gate, source, and/or drain regions. Any suitable contacts 60 and 65 may be formed using conventional materials and semiconductor fabrication techniques. For example, in embodiments, the contacts 60 and 65 comprise a liner and conductive material, and are formed by first forming contact holes in the ILD layer 55 down to, or slightly below, the upper surfaces of the gates 25 and 30 and the first and the second doped regions 35, 40, 45, and 50. The liner is formed on the exposed surfaces of the contact holes. The liner may comprise, for example, Ta, TaN, Ti, TiN, Ru, RuN, W, WN, or any other material that can serve as a barrier to prevent conductive material from diffusing there through. Next, the contact holes are filled with a conductive material such as, for example, Cu, W, Al, Cu alloys, etc.

As also depicted in FIG. 3, wiring layers 70 and 75 may be formed on the ILD layer 55 connected to the contacts 60 and 65. Any suitable wiring layers 70 and 75 may be formed using conventional materials and semiconductor fabrication techniques. For example, in embodiments, the wiring layers 70 and 75 may be deposited and patterned using conventional complementary metal-oxide-semiconductor (CMOS) technologies comprising a liner and conductive material, as described above with respect to the contacts 60 and 65. Following formation of the wiring layers 70 and 75 in the ILD layer 55, an ILD layer 80 may be deposited on the exposed surfaces and planarized, and contacts 85 and 90 may be formed in the ILD layer 80, much as described above with respect to the ILD layer 55.

Figure 4A:
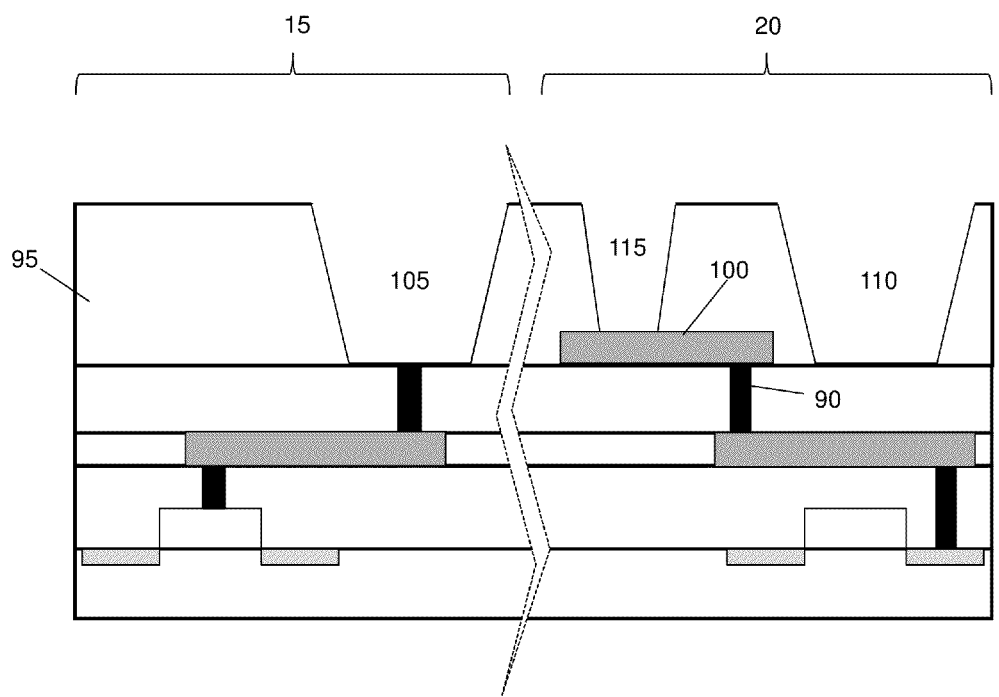

As shown in FIG. 4a, an ILD layer 95 may be deposited on the exposed surfaces and planarized, much as described above with respect to the ILD layer 55. In embodiments, the ILD layer 95 may be formed with a thickness of 1-10 μm. However, the invention is not limited to these dimensions, and the ILD layer 95 may have any desired thicknesses. Furthermore, wiring layer 100 is formed in the ILD layer 95 connected to the contact 90 as a part of the reference electrode 20, much as described above with respect to wiring layers 70 and 75.

Figure 4B:
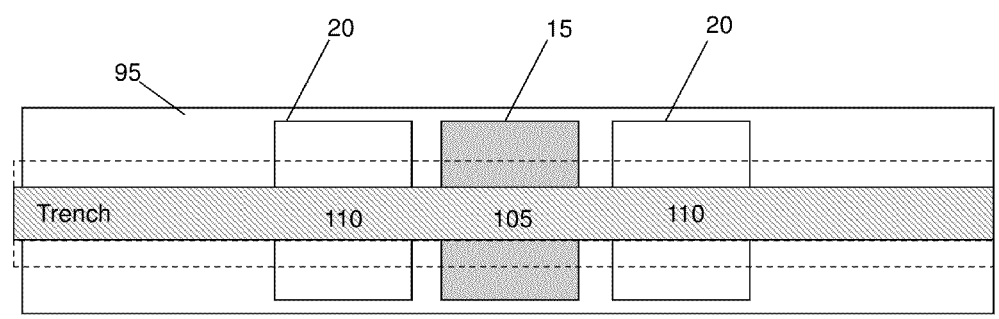

FIGS. 4a and 4b also show the formation of trenches 105 and 110 (e.g., the trenches 105 and 110 comprise a microfluidic channel) in the ILD layer 95. The trenches 105 and 110 may be formed using conventional semiconductor fabrication techniques, such as etching the ILD layer 95 through a mask, which may be a hard mask or a photoresist. For example, the mask may be formed by applying a photoresist material on the ILD layer 95, exposing, and developing the photoresist material to form a pattern on the ILD layer 95. An etch process comprising a directional etch having a chemistry that selectively removes material of the ILD layer 95 may be performed to remove a portion of the ILD layer 95 that is not protected by the mask. In particular, the patterning selectively removes a portion of the ILD layer 95 in order to expose a portion of a surface of ILD layer 80 as a part of the gate electrode 15 and the reference electrode 25, and the contact 85 as a part of the gate electrode 15. The etch process may comprise a reactive ion etch (RIE), for example.

FIGS. 4a and 4b also show the formation of trench 115 in the ILD layer 95 as a part of the reference electrode 20. The trench 115 may be formed using conventional semiconductor fabrication techniques, such as etching the ILD layer 95 through a mask, much as described above with respect to trenches 105 and 110. In particular, the patterning selectively removes a portion of the ILD layer 95 in order to expose a portion of a surface of wiring layer 100 as a part of the reference electrode 20.

Figure 5:
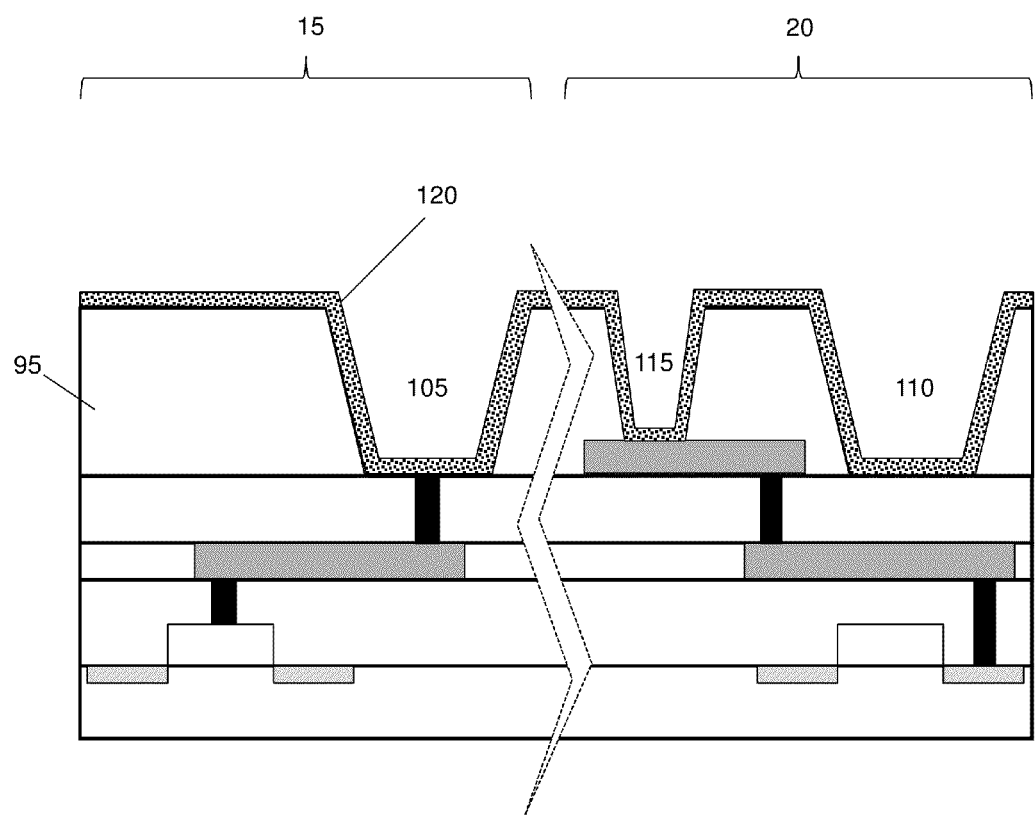

As shown in FIG. 5, a seed layer 120 may be formed over the ILD layer 95. Particularly, the seed layer 120 may be formed by selectively sputtering (e.g., physical vapor deposition (PVD)) a metal film over the ILD layer 95. In embodiments, the seed layer 120 may be comprised of chromium, and may have a thickness of about 1,000 Å. However, the invention is not limited to these materials or dimensions, and the seed layer 120 may be comprised of any desired materials in any desired thicknesses.

Figure 6:
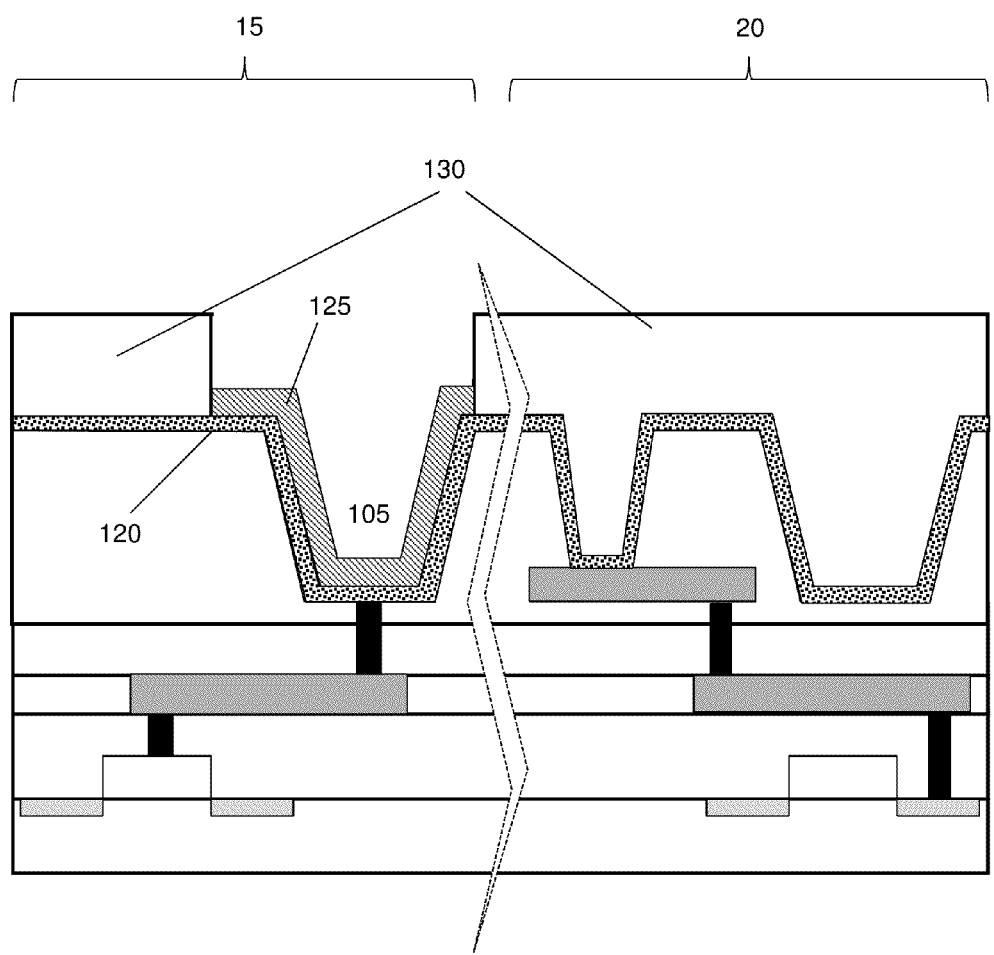

As shown in FIG. 6, a metal layer 125 may be selectively formed over the seed layer 120. Particularly, the metal layer 125 may be formed as an electroplating by selective electrodeposition on the seed layer 120. In accordance with aspects of the invention, the metal layer 125 is selectively formed over the seed layer 120 using conventional materials and semiconductor fabrication techniques, such as using a hard mask or a photoresist. In particular, a resist mask 130 may be formed on the seed layer 120 such that the metal layer is only electroplated to the seed layer 120 in the area of the trench 105 as a part of the gate electrode 15. In embodiments, the metal layer 125 may be comprised of gold, and may have a thickness of about 1,000-10,000 Å. However, the invention is not limited to these materials or dimensions, and the metal layer 125 may be comprised of any desired materials in any desired thicknesses.

Figure 7:
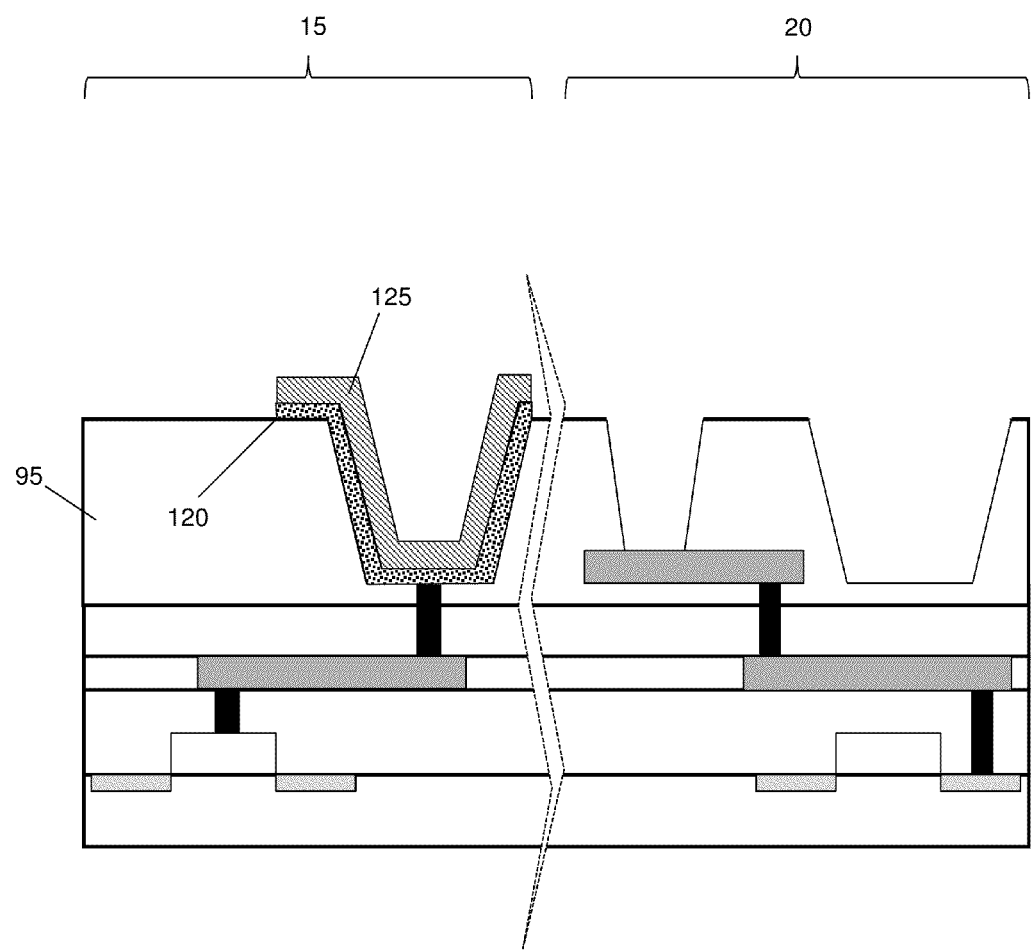

As shown in FIG. 7, once the metal layer 125 is formed, the resist mask 130 may be removed through conventional semiconductor fabrication techniques (e.g., an ashing process). In embodiments, the exposed seed layer 120 may then be selectively etched such that the seed layer 120 is removed from all areas of the gate electrode 15 and the reference electrode 20 except for under the metal layer 125. For example, a liquid-phase ("wet") etchant may be used that attacks the composition of the seed layer 120, but does not attack the composition of the metal layer 125.

Figure 8:
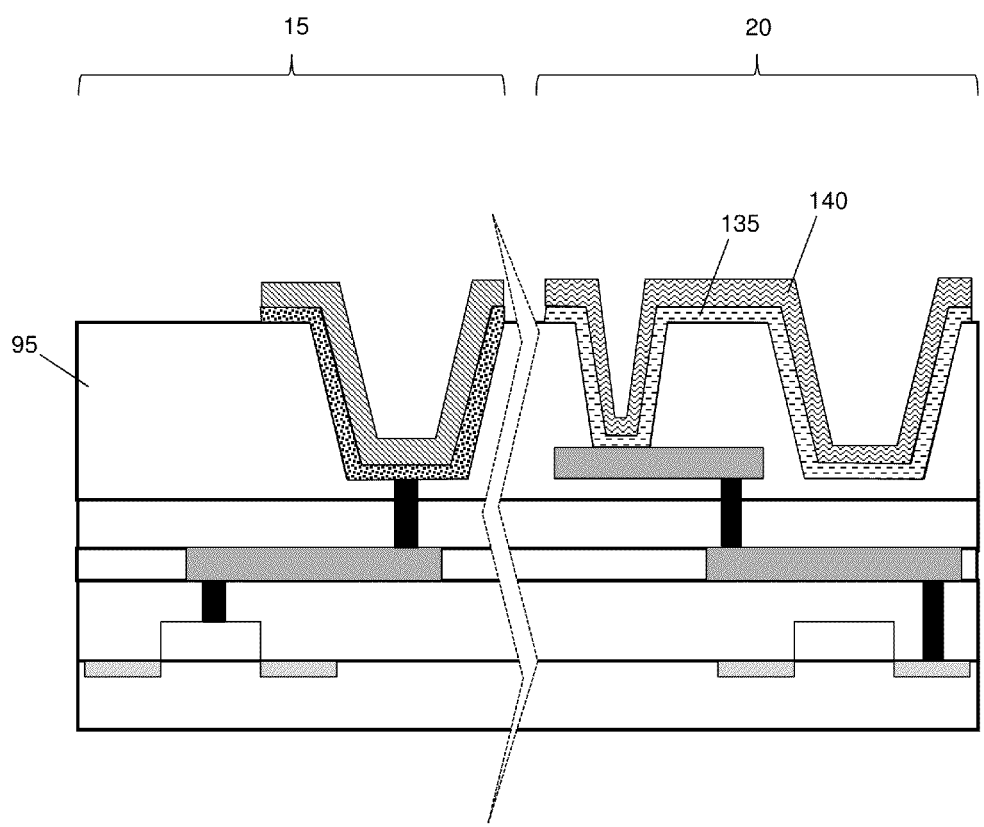

As shown in FIG. 8, a barrier layer 135 may be formed over the ILD layer 95 as a part of the reference electrode 20 using conventional materials and semiconductor fabrication techniques. Particularly, the barrier layer acts as a diffusion barrier and may be formed by selectively sputtering (e.g., physical vapor deposition (PVD)) any refractory metals or alloys thereof over the ILD layer 95 as a part of the reference electrode 20.

FIG. 8 also shows a metal layer 140 selectively formed over the barrier layer 135 as a part of the reference electrode 20. Particularly, the metal layer 140 may be formed by sputtering (e.g., PVD) a metal film over the gate electrode 15 and the reference electrode 20, and then selectively etching the metal layer 140 such that the metal layer 140 is removed from all areas of the gate electrode 15. For example, a liquid-phase ("wet") etchant may be used with conventional semiconductor fabrication techniques. In embodiments, the metal layer 140 may be comprised of silver, and may have a thickness of about 1,000-10,000 Å. However, the invention is not limited to these materials or dimensions, and the metal layer 140 may be comprised of any desired materials in any desired thicknesses.

Figure 9:
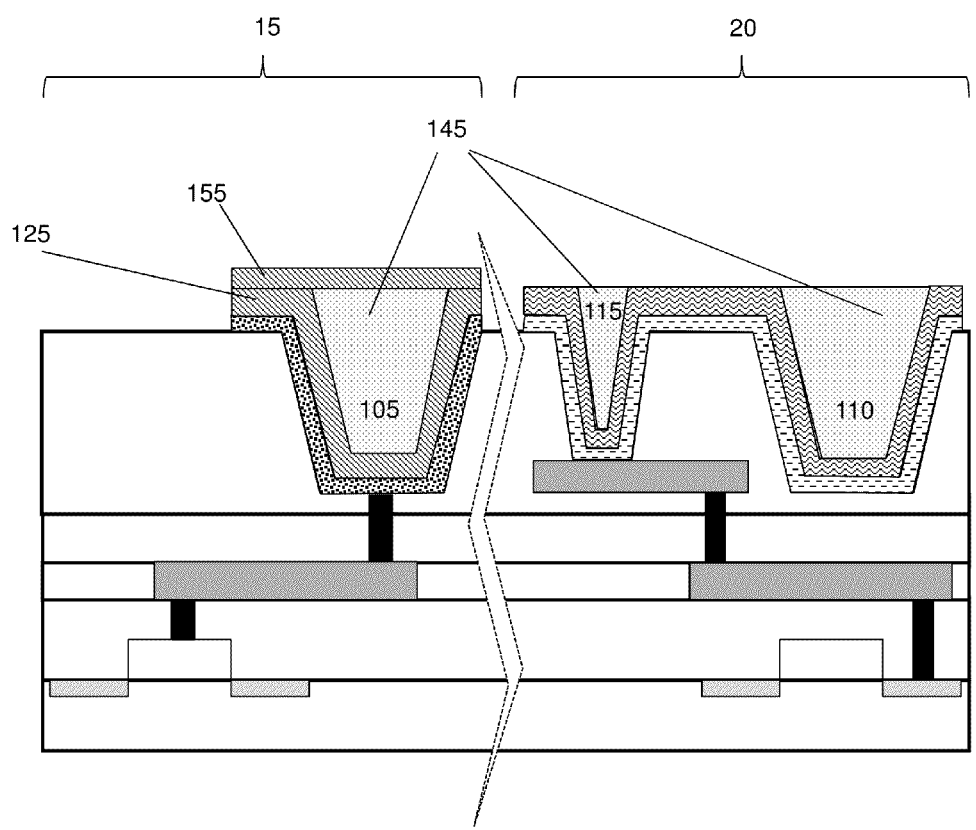

As shown in FIG. 9, the trenches 105, 110, and 115 may be filled with a sacrificial material 145. For example, the sacrificial material 145 may be deposited on the gate electrode 15 and the reference electrode 20 in any suitable manner such as CVD and may be planarized using CMP such that the sacrificial material 145 remains only in the trenches 105, 110, and 115. In embodiments, the sacrificial material may be comprised of a polymer, silicon, and/or spin-on-glass (SOG). However, the invention is not limited to these materials, and the sacrificial layer 145 may be comprised of any desired materials that can be selectively removed from the trenches.

FIG. 9 also shows a metal layer 155 selectively formed over the metal layer 125 and the sacrificial layer 145 as a part of the gate electrode 15. For example, the metal layer 155 may act as a bridge that spans the trench 105 and contacts (e.g., physically and electrically contacts) the metal layer 125 on both sides of the trench 105. In accordance with aspects of the invention, the metal layer 155 effectively increases a surface area of the gate electrode 15 in contact with a portion of the microfluidic channel (i.e., the trench 105). In embodiments, the metal layer 155 may be formed by sputtering (e.g., PVD) a metal film over the gate electrode 15, and then selectively etching the metal layer 155 such that the metal layer 155 is removed from all areas except from over the metal layer 125 and the sacrificial layer 145. For example, a wet etch or dry etch may be used with conventional semiconductor fabrication techniques. In embodiments, the metal layer 155 may be comprised of gold, and may have a thickness of about 1,000-10,000 Å. However, the invention is not limited to these materials or dimensions, and the metal layer 155 may be comprised of any desired materials in any desired thicknesses.

Figure 10A:
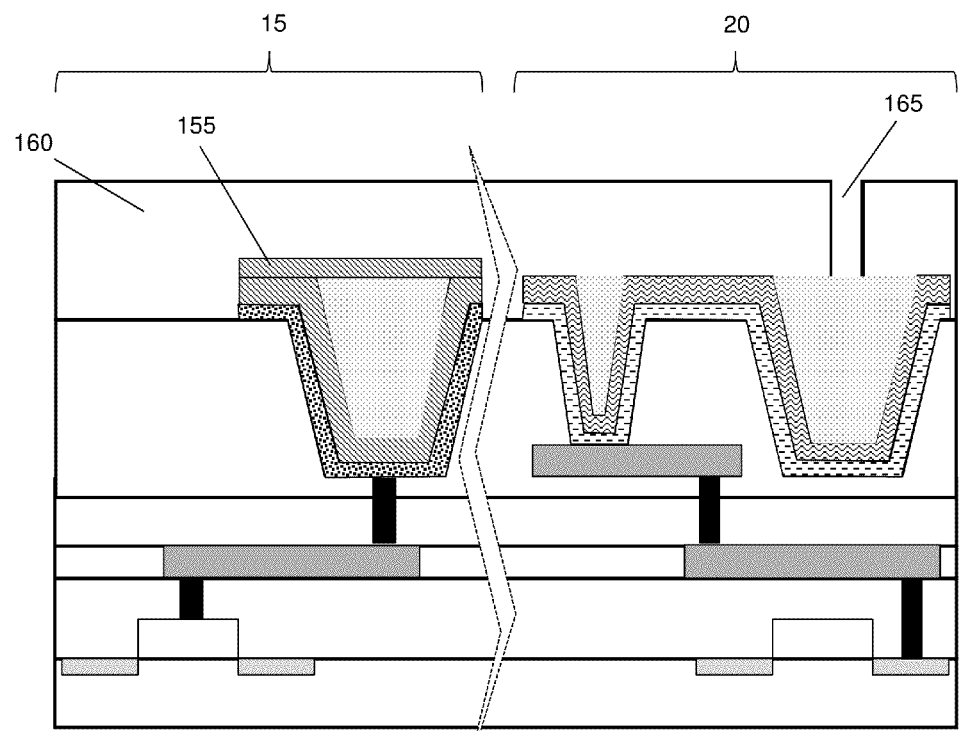

As shown in FIG. 10a, a capping layer 160 may be deposited on the exposed surfaces of the gate electrode 15 and the reference electrode 20, and planarized using e.g., CMP. In embodiments, the capping layer 160 may comprise any suitable capping material, for example, $SiO_2$ or SiN. The capping layer 160 may be deposited in any suitable manner such as low temperature CVD and may be planarized using CMP. In embodiments, the capping layer 160 may have a thickness of about 0.5-10 μm; however, the invention is not limited to these materials or dimensions, and the capping layer 160 may be comprised of any desired materials in any desired thicknesses.

Figure 10B:
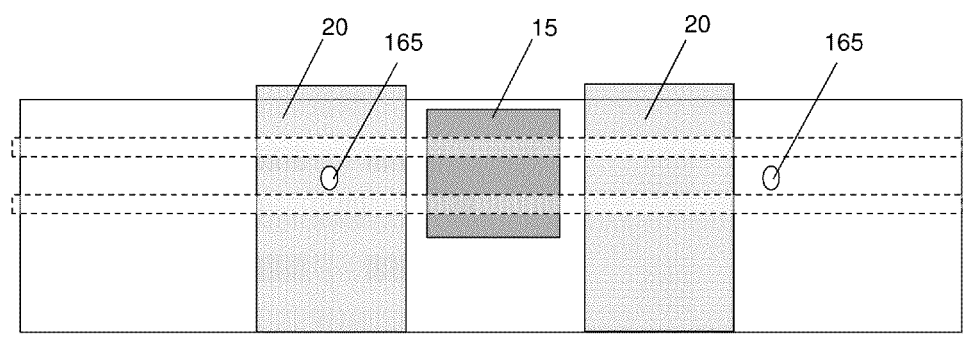

FIGS. 10a and 10b further show the formation of a vent hole 165 in the capping layer 160. For example, in embodiments, the vent hole 165 is formed in the capping layer 160 down to, or slightly below, the upper surface of the sacrificial material 145 in the trench 110 using conventional semiconductor fabrication techniques. In accordance with aspects of the invention, the vent hole 165 is not formed through the metal layer 155 and is only formed in the trench 110 outside of the area of the gate electrode 15. However, the invention is not limited to this arrangement of a single vent hole 165, and may comprise any various arrangements of any desired number of vent holes.

Figure 11:
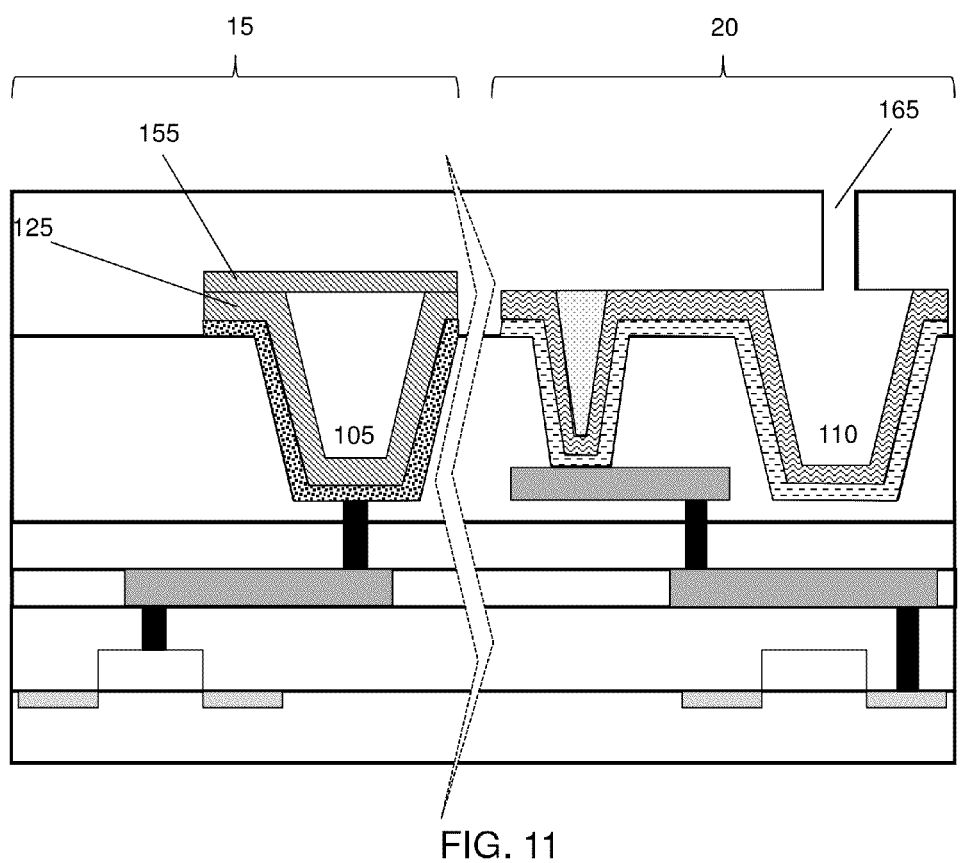

As shown in FIG. 11, the sacrificial material 145 may be removed through the vent hole 165 from the trenches 105 and 110 using conventional semiconductor fabrication techniques. For example, the sacrificial material 145 may be removed from both trenches 105 and 110 through the vent hole 165 in the trench 110 because the trenches 105 and 110 are connected as a microfluidic channel. In embodiments, if the sacrificial material 145 is comprised of SOG, then the sacrificial material 145 may be removed using a liquid-phase ("wet") etchant. Further, if the sacrificial material 145 is comprised of a polymer, then the sacrificial material 145 may be removed using plasma ashing, e.g., oxygen plasma. In addition, if the sacrificial material 145 is comprised of silicon, then the sacrificial material 145 may be removed using plasma ashing, e.g., fluorine plasma. In accordance with aspects of the invention, the removal of the sacrificial material 145 from the trenches 105 and 110 leaves the trench 105 as a part of the gate electrode 15 surrounded by metal layers 125 and 155, and the trench 110 as a part of the reference electrode 20 surrounded by the metal layer 140 and the cap layer 160.

Figure 12A:
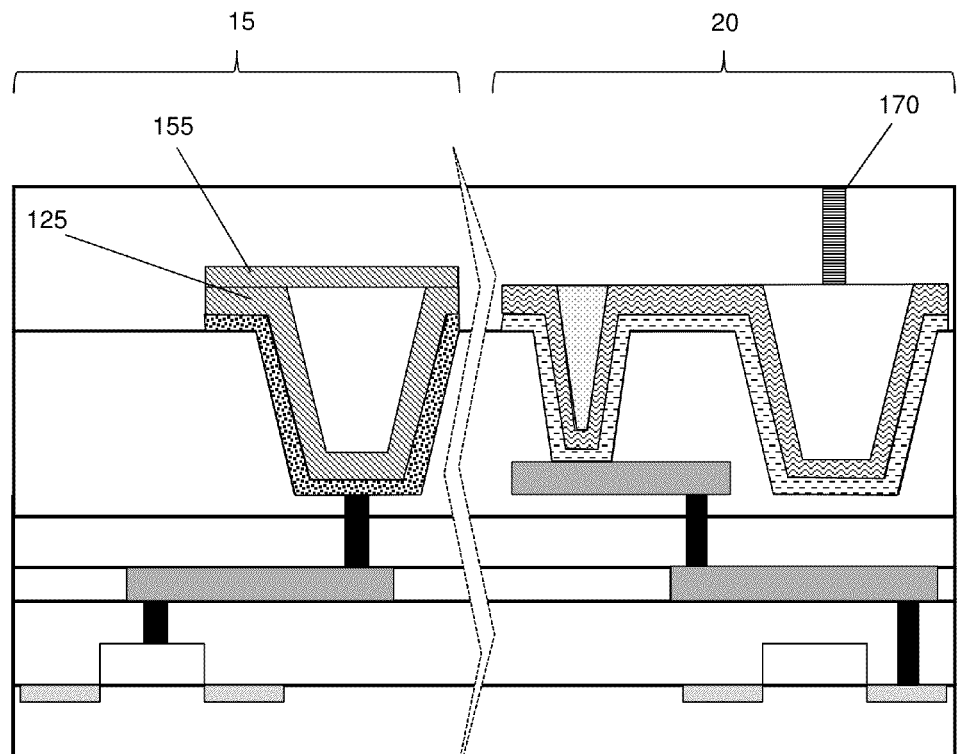

As shown in FIG. 12a, a plug 170 may be deposited in the vent hole 165, and planarized. In embodiments, the plug 170 may comprise any suitable non-conformal plugging material, for example SiN. The plug 170 may be deposited in any suitable manner such as CVD and may be planarized using CMP.

Figure 12B:
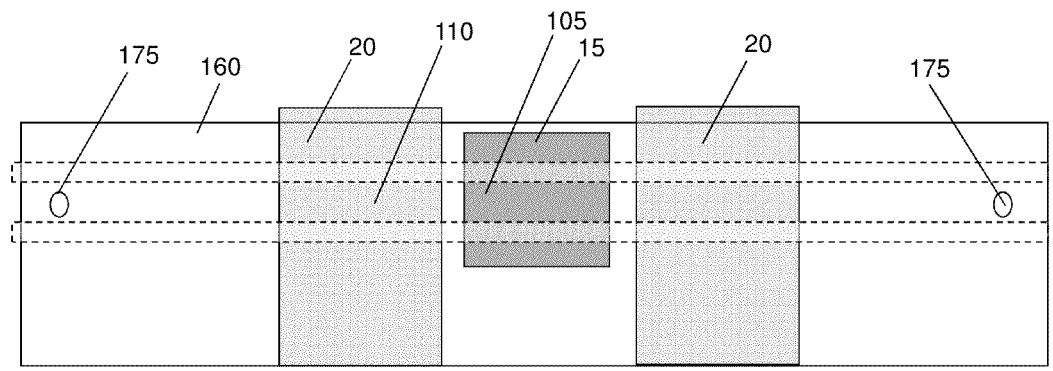

FIG. 12b shows the formation of fluid entry ports 175 in the capping layer 160. For example, in embodiments, the fluid entry ports 175 are formed in the capping layer 160 down into the trench 110 using conventional semiconductor fabrication techniques. In accordance with aspects of the invention, the fluid entry ports 175 provide a means for filling the trenches 105 and 110 (e.g., the microfluidic channel) with the measurement solution for testing purposes. However, the invention is not limited to two fluid entry ports 175 and may comprise any desired number of fluid entry ports and any various arrangements.

In accordance with aspects of the invention, the reference electrode 20 sets a potential of the electrolyte in the measurement solution for a base threshold voltage ($V_t$) such that the gate electrode 15 can then be used to determine a change in threshold voltage ($V_t$). Advantageously, the gate electrode 15 is formed such that it is surrounded by metal layers 125 and 155 (e.g., metal layer 155 acts as a bridge spanning trench 105 and contacting metal layer 125 on both sides of the trench 105), which increases the surface area of the gate electrode 15 being exposed to the measurement solution and enables greater molecular recognition events such as the hybridization and interaction of the charged biomolecules on the gate electrode 15. Thus, an increased measurable shift of the threshold voltage ($V_t$) for the biosensor 5 is readily detectable.

Figure 13A:
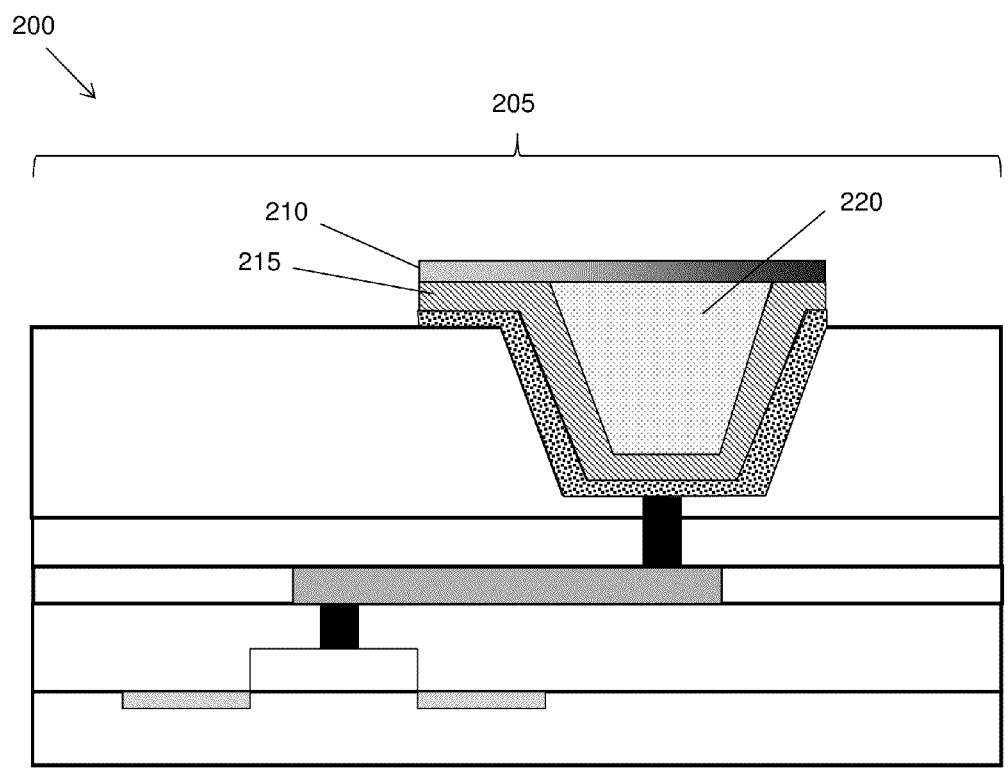

As shown in FIG. 13a, in alternative embodiments, an inductive biosensor 200 may be formed using many of the same processes as described herein with respect to the biosensor 5. However, the formation of the reference electrode 20 as performed with respect to the biosensor 5 is not necessary for the formation of the inductive biosensor 200. Particularly, the gate electrode 205 is formed much the same way as described herein with respect to gate electrode 15 up until formation of the metal layer 155.

Figure 13B:
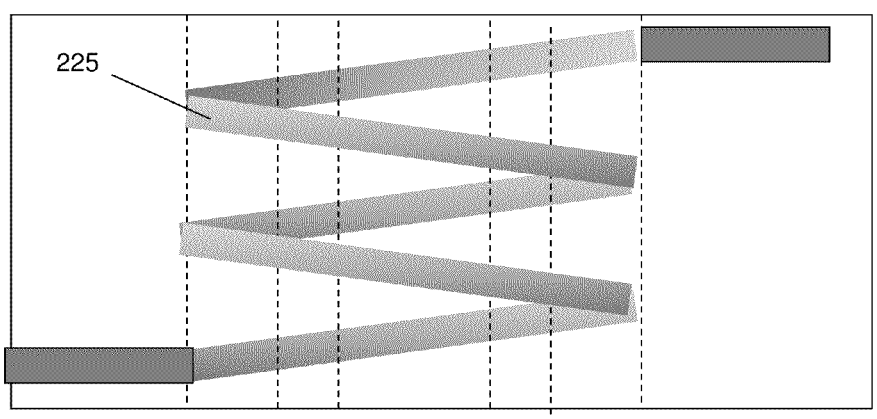

For example, as shown in FIGS. 13a and 13b, the metal layer 210 may be selectively formed over the metal layer 215 and the sacrificial layer 220 as a part of the gate electrode 205. In embodiments, the metal layer 210 may be formed by selectively sputtering (e.g., PVD) a metal film over the gate electrode 205, and then selectively etching the metal layer 210 such that the metal layer 210 is removed from all areas except from over the metal layer 215 and the sacrificial layer 220. For example, a liquid-phase ("wet") etchant may be used with conventional semiconductor fabrication techniques. The metal layer 210 is formed using the above-described processes in a spiral pattern 225, e.g., as a spiral inductor. In embodiments, the metal layer 210 may be comprised of gold, and may have a thickness of about 1,000-10,000 Å. However, the invention is not limited to these materials or dimensions, and the metal layer 210 may be comprised of any desired materials in any desired thicknesses.

Once the metal layer 210 is formed as a spiral inductor, the inductive biosensor 200 may be completed using many of the same processes as described herein with respect to the biosensor 5, e.g., forming a capping layer and removing the sacrificial material 220 to form a microfluidic channel surrounded by the metal layer 210, i.e., the spiral inductor.

Advantageously, the gate electrode 205 is formed such that it is surrounded by metal layers 210 and 215, which increases the surface area of the gate electrode 205 being exposed to the measurement solution and enables greater molecular recognition events such as the hybridization and interaction of the magnetized biomolecules on the gate electrode 205. Thus, an increased measurable shift of the threshold voltage ($V_t$) for the biosensor 200 is readily detectable.

Figure 14:
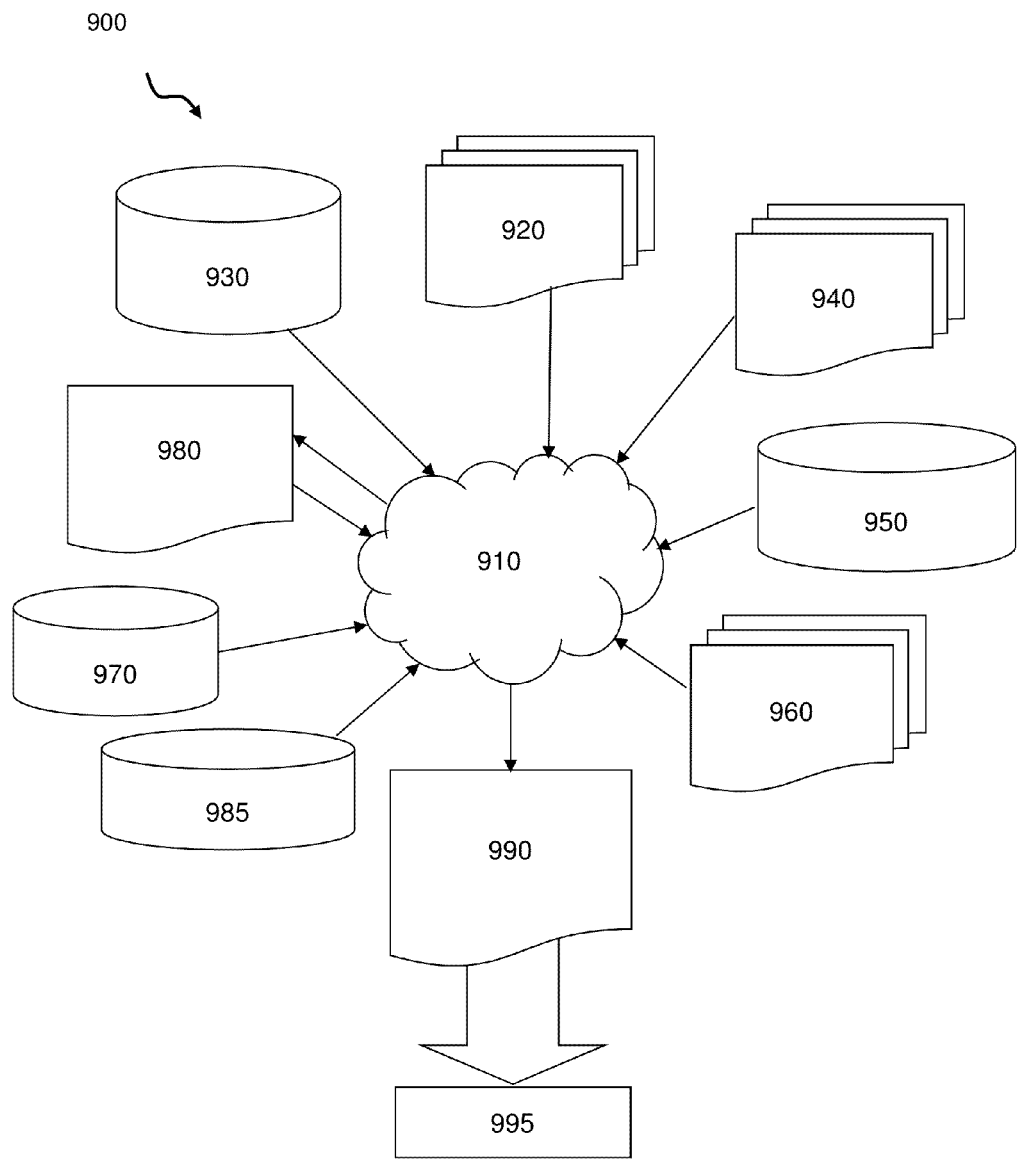
FIG. 14 is a flow diagram of a design process used in semiconductor design, manufacture, and/or test.

FIG. 14 is a flow diagram of a design process used in semiconductor design, manufacture, and/or test. FIG. 14 shows a block diagram of an exemplary design flow 900 used for example, in semiconductor IC logic design, simulation, test, layout, and manufacture. Design flow 900 includes processes, machines and/or mechanisms for processing design structures or devices to generate logically or otherwise functionally equivalent representations of the design structures and/or devices described above and shown in FIGS. 1a, 1b, 2, 3, 4a, 4b, 5-9, 10a, 10b, 11, 12a, 12b, 13a, and 13b. The design structures processed and/or generated by design flow 900 may be encoded on machine-readable transmission or storage media to include data and/or instructions that when executed or otherwise processed on a data processing system generate a logically, structurally, mechanically, or otherwise functionally equivalent representation of hardware components, circuits, devices, or systems. Machines include, but are not limited to, any machine used in an IC design process, such as designing, manufacturing, or simulating a circuit, component, device, or system. For example, machines may include: lithography machines, machines and/or equipment for generating masks (e.g. e-beam writers), computers or equipment for simulating design structures, any apparatus used in the manufacturing or test process, or any machines for programming functionally equivalent representations of the design structures into any medium (e.g. a machine for programming a programmable gate array).

Design flow 900 may vary depending on the type of representation being designed. For example, a design flow 900 for building an application specific IC (ASIC) may differ from a design flow 900 for designing a standard component or from a design flow 900 for instantiating the design into a programmable array, for example a programmable gate array (PGA) or a field programmable gate array (FPGA) offered by Altera® Inc. or Xilinx® Inc.

FIG. 14 illustrates multiple such design structures including an input design structure 920 that is preferably processed by a design process 910. Design structure 920 may be a logical simulation design structure generated and processed by design process 910 to produce a logically equivalent functional representation of a hardware device. Design structure 920 may also or alternatively comprise data and/or program instructions that when processed by design process 910, generate a functional representation of the physical structure of a hardware device. Whether representing functional and/or structural design features, design structure 920 may be generated using electronic computer-aided design (ECAD) such as implemented by a core developer/designer. When encoded on a machine-readable data transmission, gate array, or storage medium, design structure 920 may be accessed and processed by one or more hardware and/or software modules within design process 910 to simulate or otherwise functionally represent an electronic component, circuit, electronic or logic module, apparatus, device, or system such as those shown in FIGS. 1a, 1b, 2, 3, 4a, 4b, 5-9, 10a, 10b, 11, 12a, 12b, 13a, and 13b. As such, design structure 920 may comprise files or other data structures including human and/or machine-readable source code, compiled structures, and computer-executable code structures that when processed by a design or simulation data processing system, functionally simulate or otherwise represent circuits or other levels of hardware logic design. Such data structures may include hardware-description language (HDL) design entities or other data structures conforming to and/or compatible with lower-level HDL design languages such as Verilog and VHDL, and/or higher level design languages such as C or C++.

Design process 910 preferably employs and incorporates hardware and/or software modules for synthesizing, translating, or otherwise processing a design/simulation functional equivalent of the components, circuits, devices, or logic structures shown in FIGS. 1a, 1b, 2, 3, 4a, 4b, 5-9, 10a, 10b, 11, 12a, 12b, 13a, and 13b to generate a netlist 980 which may contain design structures such as design structure 920. Netlist 980 may comprise, for example, compiled or otherwise processed data structures representing a list of wires, discrete components, logic gates, control circuits, I/O devices, models, etc. that describes the connections to other elements and circuits in an integrated circuit design. Netlist 980 may be synthesized using an iterative process in which netlist 980 is resynthesized one or more times depending on design specifications and parameters for the device. As with other design structure types described herein, netlist 980 may be recorded on a machine-readable data storage medium or programmed into a programmable gate array. The medium may be a non-volatile storage medium such as a magnetic or optical disk drive, a programmable gate array, a compact flash, or other flash memory. Additionally, or in the alternative, the medium may be a system or cache memory, buffer space, or electrically or optically conductive devices and materials on which data packets may be transmitted and intermediately stored via the Internet, or other networking suitable means.

Design process 910 may include hardware and software modules for processing a variety of input data structure types including netlist 980. Such data structure types may reside, for example, within library elements 930 and include a set of commonly used elements, circuits, and devices, including models, layouts, and symbolic representations, for a given manufacturing technology (e.g., different technology nodes, 32 nm, 45 nm, 90 nm, etc.). The data structure types may further include design specifications 940, characterization data 950, verification data 960, design rules 970, and test data files 985 which may include input test patterns, output test results, and other testing information. Design process 910 may further include, for example, standard mechanical design processes such as stress analysis, thermal analysis, mechanical event simulation, process simulation for operations such as casting, molding, and die press forming, etc. One of ordinary skill in the art of mechanical design can appreciate the extent of possible mechanical design tools and applications used in design process 910 without deviating from the scope and spirit of the invention. Design process 910 may also include modules for performing standard circuit design processes such as timing analysis, verification, design rule checking, place and route operations, etc.

Design process 910 employs and incorporates logic and physical design tools such as HDL compilers and simulation model build tools to process design structure 920 together with some or all of the depicted supporting data structures along with any additional mechanical design or data (if applicable), to generate a second design structure 990.

Design structure 990 resides on a storage medium or programmable gate array in a data format used for the exchange of data of mechanical devices and structures (e.g. information stored in an IGES, DXF, Parasolid XT, JT, DRG, or any other suitable format for storing or rendering such mechanical design structures). Similar to design structure 920, design structure 990 preferably comprises one or more files, data structures, or other computer-encoded data or instructions that reside on transmission or data storage media and that when processed by an ECAD system generate a logically or otherwise functionally equivalent form of one or more of the embodiments of the invention shown in FIGS. 1a, 1b, 2, 3, 4a, 4b, 5-9, 10a, 10b, 11, 12a, 12b, 13a, and 13b. In one embodiment, design structure 990 may comprise a compiled, executable HDL simulation model that functionally simulates the devices shown in FIGS. 1a, 1b, 2, 3, 4a, 4b, 5-9, 10a, 10b, 11, 12a, 12b, 13a, and 13b.

Design structure 990 may also employ a data format used for the exchange of layout data of integrated circuits and/or symbolic data format (e.g. information stored in a GDSII (GDS2), GL1, OASIS, map files, or any other suitable format for storing such design data structures). Design structure 990 may comprise information such as, for example, symbolic data, map files, test data files, design content files, manufacturing data, layout parameters, wires, levels of metal, vias, shapes, data for routing through the manufacturing line, and any other data required by a manufacturer or other designer/developer to produce a device or structure as described above and shown in FIGS. 1a, 1b, 2, 3, 4a, 4b, 5-9, 10a, 10b, 11, 12a, 12b, 13a, and 13b. Design structure 990 may then proceed to a stage 995 where, for example, design structure 990: proceeds to tape-out, is released to manufacturing, is released to a mask house, is sent to another design house, is sent back to the customer, etc.

The method as described above is used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein. Many modifications and variations will be apparent to those of ordinary skill in the art without departing from the scope and spirit of the invention. The corresponding structures, materials, acts, and equivalents of all means or step plus function elements in the claims, if applicable, are intended to include any structure, material, or act for performing the function in combination with other claimed elements as specifically claimed. Accordingly, while the invention has been described in terms of embodiments, those of skill in the art will recognize that the invention can be practiced with modifications and in the spirit and scope of the appended claims.

What is claimed:

1. A biosensor, comprising:
a gate or electrode in a first layer;
a trench in a second layer;
a first metal layer in a first portion of the trench that is in electrical contact with the gate or the electrode; and
a second metal layer formed over the first portion of the trench and that is in electrical contact with the first metal layer,
wherein the first metal layer and the second metal layer surround the first portion of the trench and form at least a portion of a microfluidic channel for the biosensor.

2. The biosensor of claim 1, wherein:
the first metal layer and the second metal layer are in electrical contact with the gate or the electrode in a first area of a wafer of the biosensor.

3. The biosensor of claim 2, further comprising:
a second gate or electrode in the first layer;
a second trench filled with a material in the second layer; and
a third metal layer in a second portion of the trench that is in electrical contact with the second gate or the electrode.

4. The biosensor of claim 3, wherein the third metal layer is in electrical contact with the second gate or the electrode in a second area of a wafer of the biosensor.

5. The biosensor of claim 4, wherein the first area of the wafer is a gate electrode and the second area of the wafer is a reference electrode.

6. The biosensor of claim 5, wherein the first and the second metal layer comprise gold and the third metal layer comprises silver.

7. The biosensor of claim 1, wherein the second metal layer is formed in a spiral pattern to form an inductive biosensor.

8. The biosensor of claim 1, further comprising a capping layer formed over the second metal layer.

9. The biosensor of claim 8, wherein the trench is formed with the first and the second metal layers in a first area of a wafer as a first portion of the microfluidic channel.

10. The biosensor of claim 9, further comprising:
a second and third trench formed in a second area of the wafer; and
a third metal layer formed in the second and the third trench,
wherein the capping layer is formed over the second and the third trench; and
the third trench is in electrical contact with a second gate or second electrode.

11. The biosensor of claim 10, wherein the second trench is formed with the third metal layer in the second area of the wafer as a second portion of the microfluidic channel connected to the first portion of the microfluidic channel.

12. The biosensor of claim 11, wherein the first area of the wafer is a gate electrode and the second area of the wafer is a reference electrode.

* * * * *